US005565573A

United States Patent [19]

Larock

[11] Patent Number: 5,565,573
[45] Date of Patent: Oct. 15, 1996

[54] SYNTHESIS OF EPIBATIDINE AND ANALOGS THEREOF

[75] Inventor: Richard C. Larock, Ames, Iowa

[73] Assignee: Iowa State University Research Foundation, Inc., Ames, Iowa

[21] Appl. No.: 150,968

[22] Filed: Nov. 12, 1993

[51] Int. Cl.$^6$ .................................................. C07D 401/04
[52] U.S. Cl. ........................................ 546/277.4; 546/348
[58] Field of Search ................................................ 546/272

[56] References Cited

U.S. PATENT DOCUMENTS 5,314,899  5/1994  Daly et al. ............................. 514/339

OTHER PUBLICATIONS

Wade Organic Chemistry. 1987 by Prentice–Hall Inc.
Marinelli Journal of Organometallic Chemistry 368 (1989) 249–256.
Larock et al. CA 112:98074, 1989.
Thorner, Chemical Society Reviews vol. 8, No. 4, 1979, pp. 563–580.
Mar., p. 21, McGraw–Hill Book Company 1968.
Wagner and Zook, Synthetic Organic Chemistry John Wiley & Sons, Inc. 1953.
C. A. Broka, "Total Synthesis of Epibatidine," *Tet. Letters*, 34(20), 3251 (1993).
H. Brunner et al., "Asymmetric Catalysis 72.[1] Enantioselective Hydroarylation of Norbornene and Norbornadiene with Palladium(II) Acetate/Phosphine Catalysts," *Synthesis*, No. 12, 1121 (Dec. 1991).
S. C. Clayton et al., "A Total Synthesis of (±)–Epibatidine," *Tet. Letters*, 34(46), 7493 (1993).
E. J. Corey et al., "Stereocontrolled Total Synthesis (+)–(–)–Epibatidine," *J. Org. Chem.*, 58(21), 5600 (1993).
S. R. Fletcher et al., "The Synthesis of (+) and (–)–Epibatidine," *J. Chem. Soc., Chem. Commun.*, 1216 (1993).
D. F. Huang et al., "A Versatile Total Synthesis of Epibatidine and Analogs," *Tet. Letters*, 34(28), 4477 (1993).
R. C. Larock et al., "Palladium–catalysed Intermolecular Arylation and Alkenylation of Bicyclic Alkenes," *J. Chem. Soc., Chem. Commun.*, Issue 18, 1368 (1989).
T. F. Spande et al., "Epibatidine: A Novel (Chloropyridyl)azabicycloheptane with Potent Analgesic Activity from an Ecuadoran Poison Frog," *J. Am. Chem. Soc.*, 114, 3475 (1992).

*Primary Examiner*—Jane Fan
*Attorney, Agent, or Firm*—Schwegman, Lundberg, Woessner & Kluth, P.A.

[57] ABSTRACT

The present invention provides a method to prepare epibatidine or an analog thereof comprising reacting a bicyclic olefin or diene, such as an azanorbornene, with an aryl or heteroaryl halide or triflate in the presence of a catalytic amount of Pd(O) and a formate salt.

10 Claims, No Drawings

SYNTHESIS OF EPIBATIDINE AND ANALOGS THEREOF

BACKGROUND OF THE INVENTION

Epibatidine (exo-2-(6-chloro-3-pyridinyl)-7-azabicyclo [2.2.1]heptane) is isolated in minute amounts from an Ecuadoran poison frog Epipedobates tricolor. Its structure and limited biological properties were first reported in 1992 [see *J. Am. Chem. Soc.*, 114, 3475 (1992)]. It is described as a non-opioid analgesic with about 200–500 times the analgesic properties of morphine. It is clear that epibatidine and/or analogs have tremendous pharmaceutical potential for the treatment of pain. The structure of epibatidine is shown as formula I, below:

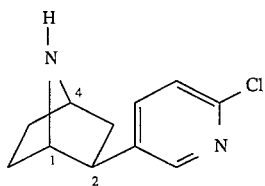

In 1993, four syntheses of epibatidine were reported, including two that are enantioselective [*J. Chem. Soc., Chem. Commun.*, 1216 (1993); *Tetrahedron Lett*, 34, 4477 (1993); *Tetrahedron Lett.*, 34, 3251 (1993); *J. Am. Chem. Soc.*, 58, 5600 (1993)]. All of these syntheses are rather lengthy, requiring 4–17 steps, and all involve as a key step the cyclization of a cyclohexane-containing amine. It is clear that these relatively inefficient syntheses are not practical for the industrial preparation of epibatidine and analogs. Therefore, a need exists for new syntheses of epibatidine and analogs thereof, which are shorter and/or proceed in higher yield.

SUMMARY OF THE INVENTION

The present invention provides a method for the one-step synthesis of epibatidine and bioactive analogs thereof, of the general formula II:

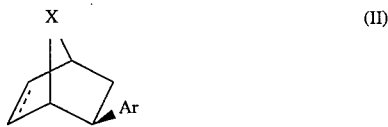

wherein X is $CH_2$, $CH_2CH_2$, O or NR, wherein R is H, Ar $(C_1-C_{12})$alkyl, $(C_6-C_{12})$arylalkyl, $SO_2R^1$, $CO_2R^1$ or $COR^1$, wherein $R^1$ is H, Ar, $CF_3$, $(C_1-C_{12})$alkyl, or $(C_6-C_{12})$arylalkyl, and wherein Ar is $(R^2)$ $(R^3)$ $(C_6-C_{18})$aryl, or a (5-10)-membered heteroaromatic ring comprising 1–3 N, S, or nonperoxide O ring atoms and substituted by $(R^2)$ $(R^3)$; wherein each of $R^2$ and $R^3$ is H, $(C_1-C_{12})$alkyl, halo, nitro, cyano, hydroxy, hydroxy$(C_1-C_6)$alkyl, —$(C=O)R^4$, $CO_2R^4$, —$CO_2N(R^5)$ $(R^6)$, —$SO(R^4)$, —$SO_2R^4$—$SR^4$, phenoxy, phenyl, $(R^5)(R^6)N$—, wherein each of $R^4$, $R^5$ and $R^6$ is H or $(C_1-C_{12})$alkyl; or $R^2$ and $R^3$ together are benzo or dioxymethylene. The bicyclic skeleton may be saturated or contain a carbon-carbon double bond where the dashed bond is indicated, i.e., the dashed bond may be absent or present (together with the adjacent $(C_5-C_6)$ bond, it may form a double bond).

Preferably, Ar is $(R^2)$ $(R^3)$phenyl or $(R^2)$ $(R^3)$naphthyl and $(R^2)$ $(R^3)$heteroaryl is a (5,6)-membered ring, substituted by $R^2$ and $R^3$. Preferably, one of $R^2$ and $R^3$ is H. As used herein, the term "heteroaromatic ring" includes pyridine, furan, thiophene, pyrrole, imidazole, pyrazole, oxazole, isoxazole, indole, benzofuran, benzothiophene, quinoline, isoquinoline, carbazole, isothiazole, thiazole, pyridazine, pyrimidine, and pyrazine. Most preferably, the heteroaromatic ring is pyridyl.

Preferably, the bond represented by the dashed line is absent. The wedged bond at $C_2$ indicates that the stereochemistry of the aryl (Ar) group is exo. The pharmaceutically acceptable salts of the compounds of formula II are also within the scope of the present invention, i.e., acid addition salts of amino group(s) and/or carboxate salts.

The present method employs the following reaction:

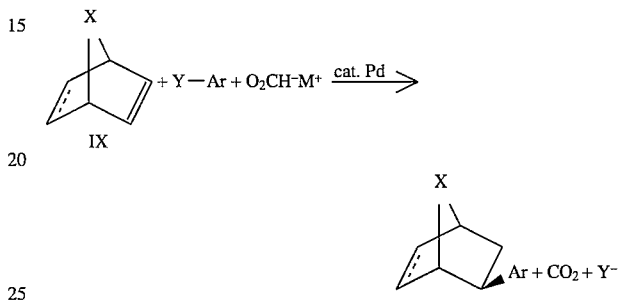

wherein a bicyclic alkene or diene (IX) with X as defined above is reacted with an aromatic halide or triflate (ArY) wherein Y=Br, I or $O_3SCF_3$ and Ar is as defined above, in the presence of a palladium catalyst and a formate salt $(O_2CH^-M^+)$, wherein $M^+$ is preferably one equivalent of an alkali metal cation, a trialkylammonium cation or a pyridinium cation.

This short, highly efficient process expands upon the methodology developed by Larock and Johnson [see *J. Chem. Soc., Chem. Commun.*, 1368 (1989) and the M. S. thesis of P. L. Johnson, Iowa State University (1989)] using a palladium catalyst and an alkali metal formate salt, or one can employ a palladium catalyst and a trialkylammonium formate salt. See Cacchi et al., *J. Organomet. Chem*, 368, 249 (1989).

Naturally occurring epibatidine is the (+)-enantiomer, 1R, 4S, 2R-(6-chloro-3-pyridinyl)-7-aza-bicyclo[2.2.1]heptane, and the present method can be readily adapted to provide primarily one enantiomer of epibatidine or its analogs by adding a catalytic amount of a chiral ligand. This approach has been used by Brunner and Kramler in the enantioselective cross-coupling of iodobenzene and norbornene [*Synthesis*, 1121 (1991)]. Unfortunately, they used rather flexible diphosphine ligands which impart enantioselectivities of only 37% or less.

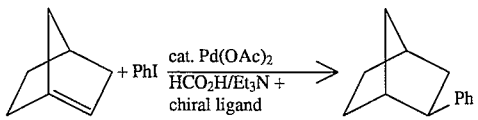

In the present method, the less rigid chelating ligands used by Brunner, such as Norphos and Chiraphos can be employed to enantioselectively produce epibatidine and analogs, but better results are obtained using more rigid, hindered chiral ligands, such as binap, bis(oxazoline) ligands and others as described hereinbelow.

Also shown in Scheme I, wherein Y, X and Ar are as described above, the reaction to form II mechanistically is believed to involve palladium(O) insertion into the Ar-Y bond to generate ArPdY which adds to the C—C double bond of IX to produce intermediate III which undergoes formate displacement to form palladium complex IV. Complex IV then loses $CO_2$ and reductively eliminates Pd to form the product.

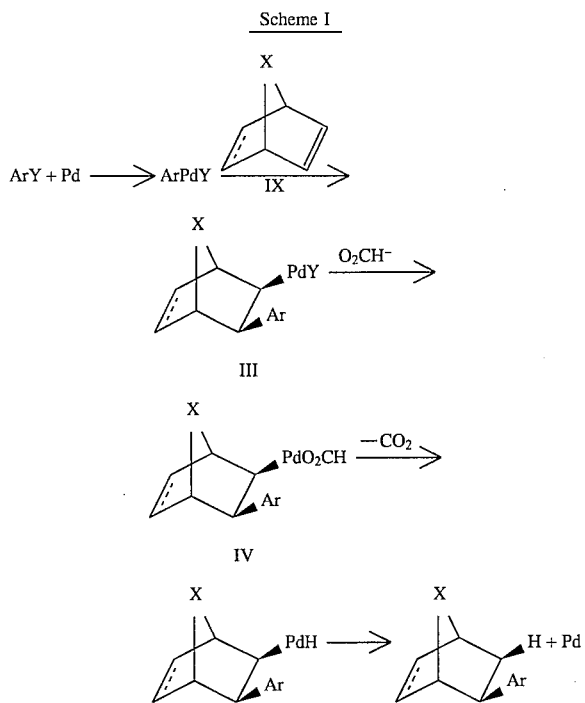

Scheme I

DETAILED DESCRIPTION OF THE INVENTION

A wide variety of bicyclic alkenes or dienes (IX) can be used in the present process. Prior work [*J. Chem. Soc., Chem. Commun.*, 1368 (1989)] established that norbornene, norbornadiene, bicylo[2.2.2]octene and a substituted 7-oxanorbornene all react well in the general system of Scheme I. 7-Azanorbornene and 7-azanorbornadiene and nitrogen-substituted derivatives of these compounds are readily available [see *J. Org. Chem.*, 40, 2551 (1975); *Chem. Ber.*, 124, 791 (1991); *Angew. Chem., Int. Ed. Engl.*, 21, 778 (1982)]. A wide variety of substituents R may be located on the nitrogen moiety of the 7-azanorbornene and 7-azanorbornadiene, including R=H, $(C_1-C_{12})$alkyl, $(C_6-C_{18})$aryl, 5- to 10-membered heteroaryl, $(C_6-C_{12})$arylalkyl, $CO_2R^1$, $SO_1R^1$ or $COR^1$ ($R^1$=H, $(C_1-C_{12})$alkyl, $CF_3$, $(C_6-C_{18})$aryl, 5- to 10-membered heteroaryl or $(C_6-C_{12})$arylalkyl). Since organopalladium-based syntheses are compatible with all of these substituents, there are no problems to be expected with introducing these substituents on the nitrogen moiety and carrying out the subsequent synthetic reactions. The bicyclic alkene or diene is preferably used in molar amounts equivalent to the aryl halide or triflate, but an excess of one substance or the other is sometimes desirable to improve the yield. Therefore, a mole ratio of alkene to aryl halide or aryl triflate of 5-0.2:1 may be employed.

A wide variety of substituted and unsubstituted aryl bromides, iodides and triflates (ArY=ArBr, ArI, $ArO_3SCF_3$), can be employed in the present process. The aryl group (Ar) is as defined above, e.g., Ar can be a $C_6-C_{18}$ aryl moiety, such as phenyl, naphthyl, or a heteroaromatic ring, such as pyridine, furan, thiophene, pyrrole, imidazole, pyrazole, oxazole, isoxazole, indole, benzofuran, benzothiophene, quinoline, isoquinoline, carbazole, isothiazole, thiazole, pyridazine, pyrimidine, or pyrazine. The bromide, iodide or triflate may be attached at any position on the aryl ring. A wide variety of substituents may be present on the aryl group including H, $(C_1-C_{12})$alkyl, halo (F, Cl, Br, I), $(C_1-C_{12})$alkoxy groups, aryloxy, phenoxy, phenyl, nitro, aldehyde, $(C_1-C_{13})$acyl, $CO_2H$, $(C_1-C_{12})$alkoxycarbonyl, CN, $(C_1-C_{12})$amide, sulfonyl, sulfoxyl, hydroxy, sulfide, hydroxy$(C_1-C_{12})$alkyl, amino $(NH_2)$ or $(C_1-C_{12})$mono- or dialkylamino groups. Other representative Ar-substituents are disclosed in Blaser et al. (U.S. Pat. No. 4,335,054), the disclosure of which is incorporated by reference herein. If an aryl bromide is used, the substituents on Ar are preferably electron-withdrawing. As used throughout, the term "alkyl" includes branched or straight-chain alkyl. Preferably, Ar is a heterocyclic moiety, which comprises 1–3 N, S or nonperoxide O ring atoms, including mixtures thereof. The aryl halide or triflate is typically used in amounts equivalent to the alkene.

The palladium(O) [Pd(O)] catalyst is generally employed in an amount of about 0.001–20 mol-%, preferably 0.0025–3 mol-%, based on the aryl halide or triflate. Useful catalysts include Pd(O) complexes, such as bis(dibenzylideneacetone)palladium(O), bis(methyl-isonitrile)palladium(O), bis(cyclohexylisonitrile) palladium(O), bis(isopropylisonitrile)palladium(O), bis(tert-butylisonitrile)palladium(O), bis(p-tolylisonitrile)palladium(O), bis(phenylisonitrile)palladium(O), and bis(p-methoxyphenylisonitrile)palladium(O). Amongst the above compounds, bis(dibenzylideneacetone)palladium(O) is preferred.

The palladium(O) catalyst may also preferably be generated by adding a palladium(II) salt to the reaction mixture which is then reduced to palladium(O) in situ. Suitable palladium(II) salts are $Pd(OAc)_2$, $Pd(NO_3)_2$, $PdCl_2$, $Li_2PdCl_4$, $LiPdCl_3$, $PdBr_2$, $Pd(O_2CCF_3)_2$, $PdSO_4$, $Pd(CN)_2$ and the like. Other Pd catalysts which can be used in the present method include those disclosed in Blaser et al. (U.S. Pat. No. 4,335,054). $Pd(OAc)_2$ is preferred due to its stability, ready availability and ease of handling.

These reactions are run using equivalent amounts or an excess (up to 5 mole equivalents) of alkali metal formate salts ($LiO_2CH$, $CsO_2CH$, $NaO_2CH$ or $KO_2CH$) with respect to the ArY reactant; $KO_2CH$ is the preferred salt. Alternatively, one can employ pyridinium or trialkylammonium formate salts [*J. Organomet. Chem.*, 368, 249 (1989)] which are most readily prepared by adding pyridine or a tri($C_1-C_4$)alkylamine, such as triethylamine or tri-n-butylamine, to an equivalent amount of formic acid. For aryl halides bearing electron-withdrawing groups or electron-deficient heterocycles, it is preferred to carry out the present method with lesser amounts of formate salt, due to reduction of the aryl substrate to the corresponding arene. The preferred procedure uses only about one equivalent of the formate salt.

A source of halide, preferably of chloride ion ($Cl^-$), is also preferably employed in the present process, and can act to increase both the reaction rates and the yields. Preferred chloride sources are tetraalkyl- or tetraarylammonium chlorides, including tetra-n-butylammonium chloride (n-$Bu_4NCl$), tetraalkyl- or tetraaryl-phosphonium chlorides and alkali metal chlorides, including lithium chloride. LiCl and n-$Bu_4NCl$ are the preferred chloride sources, but other sources of $Cl^-$ are essentially equally effective. This reagent is preferably employed in equimolar amounts with respect to the other starting materials, although the precise amount is not critical.

These reactions can be effected enantioselectively by adding one or more chiral chelating ligands in catalytic (0.001–20 mol-%) amounts. One can use the less rigid, chelating ligands disclosed by Brunner [*Synthesis*, 1121 (1991)], such as Norphos and Chiraphos (bis(diphenyl-phosphino)-butane-(+) or (−)), but better results are obtained using more rigid hindered chiral ligands, such as Binap (commercially available from Aldrich Chem. Co., Milwaukee, Wis.), bis(oxazoline) ligands [see *Helv. Chim. Acta*, 74, 232 (1991); *Helv. Chim. Acta*, 74, 1 (1991); *Synlett*, 257 (1991); *Tetrahedron Lett.*, 31, 6005 (1990); *J. Am. Chem. Soc.*, 113, 726 and 728 (1991); *Angew. Chem., Int. Ed. Engl.*, 30, 542 (1991)], semicorrin ligands [*Helv. Chim. Acta*, 71, 1541 (1988); *Tetrahedron*, 48, 2143 (1992)], aryl phosphorus-containing oxazole ligands [*Tetrahedron Lett.*, 34, 3149 (1993); *Tetrahedron Lett.*, 34, 1769 (1993)], bithiazoline ligands [*Synlett* 257 (1991)], and pyridineoxazoline ligands [*Tetrahedron: Asymmetry*, 4, 143 (1993)]. The preferred ligands are chiral bis(phosphines) such as Binap (2,2'-bis(diphenyl-phosphino)-1,1'-binaphthyl) and the oxazoline ligands. See also Henri Brunner in *Topics in Stereochemistry*, Vol. 18, E. Eliel et al., eds., J. W. Wiley-Interscience (1988) at pages 129–247; *Synthesis*, pages 503–517 (1992); and *Chem. Rev.*, 89, 1581 (1989).

Preferred organic solvents for use in carrying out the present method are those which are polar. These include ($C_1$–$C_4$) alkanols, tetrahydrofuran (THF), acetonitrile, dialkyl ethers, glycol ethers, formamide, N,N-dimethylformamide (DMF), N,N-dimethylacetamide (DMA), N-methylpyrrolidone, tetramethylurea, hexamethylphosphoramide and dimethylsulfoxide. DMF or DMA are the preferred solvents.

These reactions are carried out at temperatures ranging from room temperature (25° C.) up to about 120° C., most preferably at the lowest possible temperature at which the aryl halide or triflate will react with the palladium catalyst in a reasonable amount of time. For most reactions, room temperature for 24–72 hours up to about 4–5 days provide the desired reaction conditions, although higher temperatures may be used to increase the rate of reaction.

After the reactions are finished, the reaction mixtures are processed using standard methodologies. Typically, this involves the addition of ether ($Et_2O$), washing with aqueous ammonium chloride and water, drying the mixture, evaporation of the solvent and distillation, recrystallation or column chromatography or HPLC, as appropriate. All products can be characterized by $^1H$ and $^{13}C$ NMR spectroscopy, IR spectroscopy, mass spectrometry and elemental analysis.

The present method is very versatile. A wide variety of bicyclic alkenes and dienes, and aryl bromides, iodides and triflates, including polyaromatic and heterocyclic compounds can be successfully employed as starting materials. The aryl group is observed to add stereoselectively from the exo face of the C—C double bond of compound IX to produce exo-substituted products of formula II. By employing rigid chiral chelating ligands in small amounts, one can accomplish these arylation reactions in fair to excellent enantiomeric excess, thus directly producing the chiral products.

The following examples illustrate the chemical process, but do not limit it.

EXAMPLE 1.

The epibatidine analog V was prepared in 65% yield by reacting 0.5 mmol of 3-iodopyridine, 0.5 mmol of norbornene, 0.5 mmol of n-$Bu_4NCl$ and 0.5 mmol of potassium formate in the presence of 5 mol-% $Pd(OAc)_2$ in 1.0 mL DMF in a one dram vial equipped with magnetic stirring. The reaction mixture was stirred at 25° C. for 5 days. The reaction mixture was then diluted with saturated aqueous NaCl and extracted with ether. The organic layer was dried over anhydrous $Na_2SO_4$. After removal of the solvent in vacuo, the product V was purified by flash chromatography on a silica gel column.

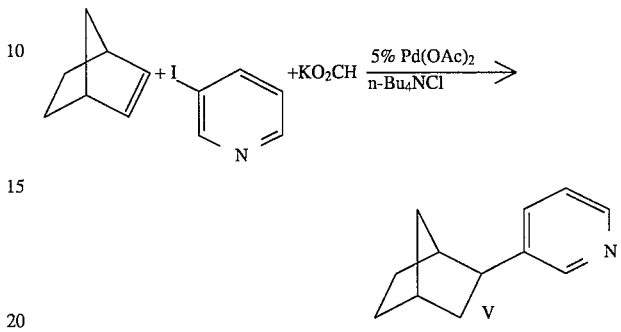

EXAMPLE 2.

The chloropyridine analog VI is prepared in similar yield by the same process.

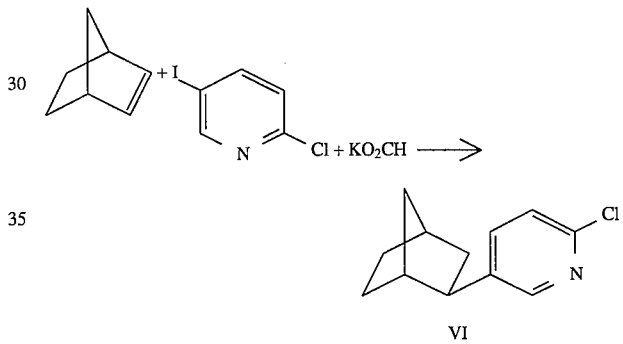

EXAMPLE 3.

Epibatidine (I) itself or its carboethoxy analog (VII) can be prepared by reacting 7-azanorbornene or its carboethoxy analog with 2-chloro-5-iodo-pyridine [*Chem. Ber.*, 58, 113 (1925)] under similar conditions. Higher yields can be obtained by using an excess of either alkene or aryl iodide.

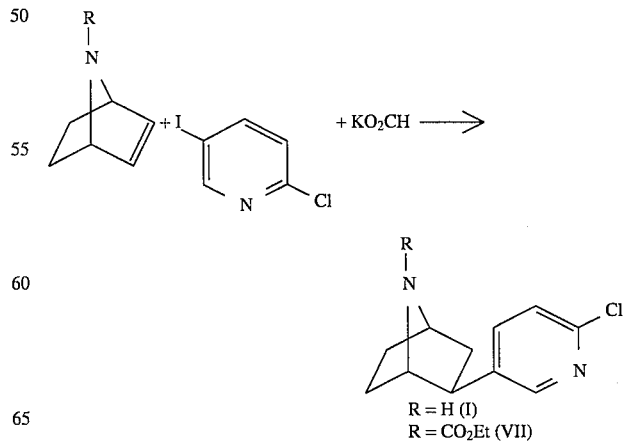

EXAMPLE 4.

The syntheses disclosed in Exs. 1–3 can be effected enantioselectively by adding 0.1–20% of a preselected chiral ligand. For example, either enantiomer of epibatidine analog V can be prepared by adding 5 or 10 mol-% of Binap or bis(oxazoline) ligand VIII to the reaction described above. The larger the amounts of the ligand, the larger the enantiomeric excess of a given enantiomer of formula II. In a similar fashion, either (+)- or (−)-epibatidine can be prepared by using either the (+)- or (−)-enantiomer of either of these ligands, respectively, in catalytic amounts. Other chiral ligands described hereinabove can also be employed in the synthesis of epibatidine and its analogs.

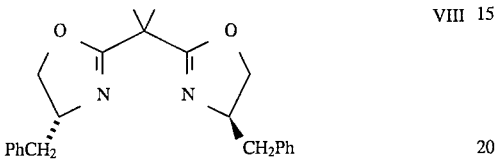

VIII

All publications, patents and patent documents cited herein are incorporated by reference herein, as though fully set forth. The invention has been described with reference to various specific and preferred embodiments and techniques. However, it should be understood that many variations and modifications may be made while remaining within the spirit and scope of the invention.

What is claimed is:

1. A method for preparing epibatidine or an epibatidine analog comprising reacting a compound of the general formula (1):

(1)

wherein X is NR, wherein R is H, $SO_2R^1$, $COR^1$ or $CO_2R^1$, wherein $R^1$ is H, Ar, $CF_3$, $(C_1–C_{12})$alkyl or $(C_6–C_{12})$arylalkyl; wherein Ar is $(R^2)(R^3)$phenyl wherein each of $R^2$ and $R^3$ is H, $(C_1–C_{12})$alkyl, halo, cyano, hydroxy, hydroxy$(C_1–C_6)$alkyl, $R^4(C=O)$—, $CO_2R^4$, $CO_2N(R^5)(R^6)$, —$SOR^4$, —$SO_2R^4$, $SR^4$, phenoxy, phenyl, or $(R^5)(R^6)N$, wherein each of $R^4$, $R^5$, and $R^6$ is H or $(C_1–C_{12})$alkyl; and the bond represented by——————is absent or is present; with a compound of the formula Y—Ar, wherein Y is Br, I or $O_3SCF_3$, and Ar is pyridyl$(R^2)(R^3)$, wherein the reaction is carried out in an organic solvent in the presence of a catalytic amount of Pd(O), a chiral chelating ligand and a formate salt, to yield an enantiomeric excess of a compound of the formula (2):

(2)

wherein the bond represented by the dashed line is present or is absent, and X and Ar are as defined above.

2. The method of claim 1 wherein R is H.

3. The method of claim 1 wherein one of $R^2$ and $R^3$ is H.

4. The method of claim 1 wherein the compound of formula II is epibatidine.

5. The method of claim 1 wherein the reaction is carried out in the presence of a source of chloride ion.

6. The method of claim 1 wherein the formate salt is an alkali metal formate salt.

7. The method of claim 1 wherein the reaction is carried out in the presence of a catalytic amount of a Pd(II) salt, which is reduced to Pd(O) in situ.

8. The method of claim 1 wherein the compound of formula (2) is (+)-1R, 4S, 2R-(6-chloro-3-pyridinyl)-7-azabicyclo[2.2.1]heptane.

9. The method of claim 1 wherein the molar ratio of the compound of formula ( 1 ) to Y-Ar is about 1:1.

10. The method of claim 1 wherein the reaction is carried out at about 25° C. for about 24–120 hours.

* * * * *